United States Patent [19]

Cheney et al.

[11] Patent Number: 5,585,544
[45] Date of Patent: *Dec. 17, 1996

[54] METHOD OF CAUSING SOMATIC HYBRIDIZATION BETWEEN TWO SPECIES OF ALGAE

[75] Inventors: Donald P. Cheney, Ipswich; Le Zhong Wang, Boston, both of Mass.

[73] Assignee: Northeastern University, Boston, Mass.

[*] Notice: The term of this patent shall not extend beyond the expiration date of Pat. No. 5,365,018.

[21] Appl. No.: 215,846

[22] Filed: Mar. 21, 1994

Related U.S. Application Data

[63] Continuation-in-part of Ser. No. 40,625, Mar. 31, 1993, Pat. No. 5,365,018.

[51] Int. Cl.$^6$ ............... A01H 1/04; A01G 7/00; C12N 15/00; C07H 1/06
[52] U.S. Cl. ............ 800/220; 800/200; 800/240; 800/DIG. 7; 47/1.4; 47/58; 435/172.1; 435/172.2; 435/240.45; 536/128; 935/93; 935/94; 935/96; 935/98
[58] Field of Search ............ 435/172.1, 172.2, 435/240.4, 240.45, 240.49; 800/200, 220, 240, DIG. 7; 47/1.4, 58; 935/91, 93, 94, 96, 98; 536/128

[56] References Cited

U.S. PATENT DOCUMENTS

| | | | |
|---|---|---|---|
| 4,199,895 | 4/1980 | Avron et al. | 47/1.4 |
| 4,869,017 | 9/1989 | Bird et al. | 47/1.4 |
| 4,996,389 | 2/1991 | Bird | 800/200 |
| 5,365,018 | 11/1994 | Cheney et al. | 800/220 |

OTHER PUBLICATIONS

Goff et al., "The Role of Secondary Pit Connections in Red Algal Parasitism", J. Phycol., 1985, pp. 483–508.
Anderson et al., "Carrageenans. IV. Variations in the Structure and Gel . . . ", J. Chem. Soc. 5:602–606, 1968, (abstract attached).
Rochas et al., "Sulfate Content of Carrageenan and Agar Determined by Infrared Spectroscopy", Botanica Marina 29:335–, 1986.
Kim et al., "Wound–Healing in Several Filamentous Red Algae, Ceramiales", The Korean Journal of Phycology, 1988, 3:15–27.
Azanza–Corrales et al., "Wound Healing in Cultured Eucheuma alvarezii var. tambalang Doty[1]", Botanica Marina, 1989, 32:229–234.
Polne–Fuller et al., "Calluses and Callus–Like Growth in Seaweeds:Induction and Culture", Hydrobiologia, 1987, 151/152:131–138.
Dawes et al., "Branch, Micropropagule and Tissue Culture of the Red Algae Eucheuma . . . ", Journal of Applied Phycology, 1991, 3:247–257.
Koslowsky et al., "Cytoplasmic Incompatibility Following Somatic Cell Fusion in Griffthsia Parcifica Klyin a Red Alga", Protoplasma, 1984, 123:7–17.
Cheney et al., "Carrageenan Analysis of Tissue Cultures and Whole Plants of Agardhiella Subulata", Hydrobiologia, 1987, 151/152:161–166.

(List continued on next page.)

Primary Examiner—David T. Fox
Assistant Examiner—Bruce R. Campell
Attorney, Agent, or Firm—Weingarten, Schurgin, Gagnebin & Hayes

[57] ABSTRACT

A method of causing somatic cell hybridization between two species of algae by growing somatic algal tissue from each of the two species of algae in close proximity, in a nutrient solution, and isolating and culturing the hybrid somatic shoots that form.

12 Claims, 11 Drawing Sheets

OTHER PUBLICATIONS

Bradley et al., "Some Effects of Plant Growth Regulators on Tissue Cultures of the Marine Red Alga Agardhiella Subulata . . . ", Hybdrobiologia, 1990, 204/205:353–360.

Goff et al., "Nuclear Transfer From Parasite to Host", Annals New York Academy of Sciences, 1987, 402–423.

Waaland, "Parasexually Produced Hybrids Between Femal and Male Plants of Griffithsia Tenuis C. Agardh . . . ", Planta, 1978, 138:65–68.

Hwang et al., "Regeneration and Sexual Differentiation of Griffithsia Japonic . . . ", J. Phycol., 1991, 27:441–447.

METHOD OF CAUSING SOMATIC HYBRIDIZATION BETWEEN TWO SPECIES OF ALGAE

RELATED APPLICATION

This application is a continuation-in-part of U.S. patent application Ser. No. 08/040,625, filed Mar. 31, 1993, now U.S. Pat. No. 5,365,018 entitled METHOD OF CAUSING SOMATIC HYBRIDIZATION BETWEEN TWO SPECIES OF ALGAE.

FIELD OF THE INVENTION

The invention relates to the field of algae culture and more particularly to the field of algal culture techniques for causing somatic Cell hybridization in algae.

BACKGROUND OF THE INVENTION

Economically important phycocolloids such as carrageenan and agar are produced by certain red algae. To extract a phycocolloid of interest, an alga is grown in a marine environment, is harvested and is processed. Different algal species may produce phycocolloids having different chemical properties and different physical characteristics, and/or may grow at an increased growth rate.

For example, carrageenan, a food industry colloid used as a clarifying agent., a suspending agent or a crystallization controlling agent, is a mixture of various length chains of sulfated disaccharide subunits. Different species of algae produce carrageenan chains having a different average number of sulphate groups per disaccharide subunit. The average sulfation per disaccharide typically varies from one (designated κ carrageenan) to three (designated λ carrageenan) sulfates per disaccharide. The intermediate value of two sulfates per disaccharide is designated ι carrageenan. *E. spinosum* produces ι carrageenan and *E. cottonii* produces κ carrageenan. The degree of sulfation determines the gel strength of the colloid extracted. A decrease in sulfation results in an increase in gel strength. Different gel strengths are desirable for different applications.

The ability to modify one species of algae by hybridizing the genetic material of a second species would permit the characteristics of the phycocolloid produced by the second species to be exhibited by the first species. Thus, for example, carrageenan having a higher than normal gel strength could be produced by an alga which typically produces a low or intermediate gel strength carrageenan. However, typically only closely related strains of a single species can sexually exchange genetic material successfully. Hence sexual hybridization has not produced commercially useful hybrid algae.

Figure 1:
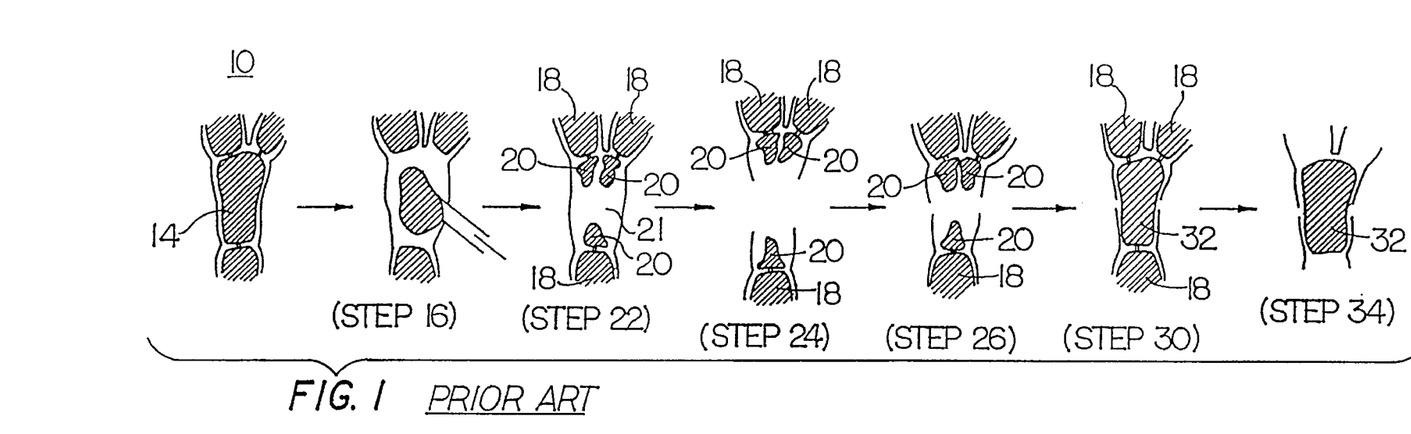
FIG. 1 is a diagrammatic representation of the steps used in one technique of fusing filamentous algae as known to the prior art.

A number of techniques have been developed to create hybrid cells by fusing somatic cells. Referring to FIG. 1, Hwang et al. in Regeneration and Sexual Differentiation Of *Griffithsia japonica* (Ceramiaceae, Rhodophyta) Through Somatic cell Fusion, *J. Phycol.* 27, 441–447 (1991), describe a method for the somatic cell fusion of cells of the filamentous red alga *Griffithsia japonica*, by wound healing, so as to form a hybrid cell. In this technique 10, a cell 14 near the apical cell is wounded (step 16) and the cytoplasm removed. Within ten hours, adjacent cells 18 produce (step 22) repair cells 20 which grow into the lumen 21 of the wounded cell 14. The wounded cell is then transacted (step 24) and the separated filaments are immobilized in close contact on an agar plate (step 26). The repair cells 20 fuse (step 30), forming a hybrid cell 32 which can then be isolated (step 34) and cultured.

Figure 1A:
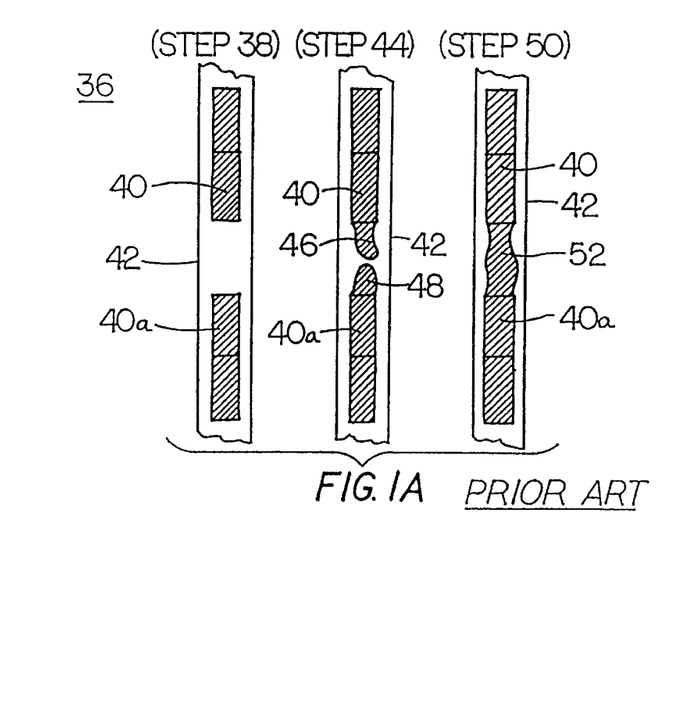
FIG. 1a is a diagrammatic representation of the steps used in another technique of fusing filamentous algae as known to the prior art.

Similarly, referring to FIG. 1a, Susan D. Waaland in Parasexually Produced Hybrids Between Female and Male Plants of *Griffithsia tenuis* C. Agardh, a Red Alga, *Planta* 138, 65–68 (1978) describes the somatic cell fusion of male and female somatic cells of the filamentous red alga *Griffithsia tenuis* grown within a thin cylinder formed from the walls of the green alga Nitella. In this technique 36, two filaments 40, 40a are positioned (step 38) within the thin cylinder 42 and allowed to grow. The upper filament 40 produces (step 44) a rhizoid 46, while the lower filament produces a repair cell 48. The rhizoid 46 and the repair cell 48 grow toward one another. Eventually the rhizoid 46 and the repair cell 48 fuse (step 50) to form a hybrid cell 52, which can then be isolated and cultured. Thus both the Hwang and Waaland techniques of somatic cell fusion are limited to the fusion of cells of filamentous algae of a single genus.

Bradley and Cheney in Some Effects of Plant Growth Regulators on tissue cultures of the marine red alga *Agardhiella subulata* (Gigartihales, Rhodophyta), *Hydrobiologica* 204/205: 353–360, 1990, describe tissue culture by the growing of projections and calluses from a disk cut from red algae but do not describe any technique for creating somatic cell hybrids.

The present invention relates to somatic cell hybridization techniques which are applicable to non-filamentous algae. The new techniques accomplish somatic cell hybridization of varieties of non-filamentous algae which have significant commercial value.

SUMMARY OF THE INVENTION

The invention relates to a method of forming somatic hybrids from two strains of non-filamentous algae. Tissue from each of the non-filamentous algae are grown in close proximity in a culture medium. The hybrid somatic shoots that form are then isolated and cultured. In one embodiment a piece of tissue from each of the non-filamentous algae strains to be hybridized are affixed in close juxtaposition in a culture medium and the hybrid heterokaryon structures which form are isolated and individually cultured. In another embodiment, a scion from one strain of non-filamentous algae is grafted onto a second strain of non-filamentous algae and the resulting graft is grown in a culture medium. The hybrid heterokaryon shoots which form from the graft are then isolated and individually cultured. In yet another embodiment, projections that grow from a cross-section of each parent plant of non-filamentous algae are grown together in close proximity and allowed to undergo nuclear exchange to produce hybrid shoots.

As used herein, two "different algal species" or "plants" refers to genetic differences; i.e., the algae may be distinguished by virtue of differing morphological, growth, temperature tolerance, or chemical characteristics, e.g., differences in appearance, isozymes, gel strengths, IR data, etc. as disclosed herein. It thus follows that a hybrid algae formed from two different algal plants or species will itself be genetically distinct from either parent species, and thus distinguishable according to morphological, growth, temperature, or chemical criteria from the parent plants. The term "plant" is also used herein to encompass a whole plant or some portion of a plant, such as a shoot.

Methods of the invention are applicable to macroscopic marine algae, preferably red algae, but also including brown algae; and in particular to non-filamentous, anatomically complex thallophytic red and brown algae. The methods are particularly applicable to red algae such as carrageenophytes and agarophytes, and to alginate-producing brown algae.

BRIEF DESCRIPTION OF THE DRAWING

Other features and benefits of the invention can be more clearly understood with reference to the specification and the accompanying drawings in which.

DESCRIPTION OF THE PREFERRED EMBODIMENT

Inventive techniques are described below for producing hybrid algal plants from two genetically distinct parent plants. According to one technique, somatic hybrids are produced by culturing sections of two parental species placed in close juxtaposition using a sterile rod. Sections so joined produce cellular projections that grow toward each other and form connections called conjunctor cells. The conjunctor cells allow for exchange of nuclei to form a heterokaryon, or a hybrid cell. The hybrid cells divide and grow into hybrid shoot primordia, which in turn grow into hybrid plants.

According to another inventive technique, two non-filamentous red algal plants of differing genetic make-up may be used to form a hybrid by allowing cellular projections to grow from a cross-section of each parent plant. The projections are cultured together to allow for nuclear exchange between the parent cellular projections. Growth of the thus-fused cell produces a heterokaryon or hybrid algae.

The examples provided below of different embodiments of the invention are meant to clearly illustrate preferred methods of carrying out the invention, and are not meant to limit the invention.

EXAMPLE 1

Figure 2:
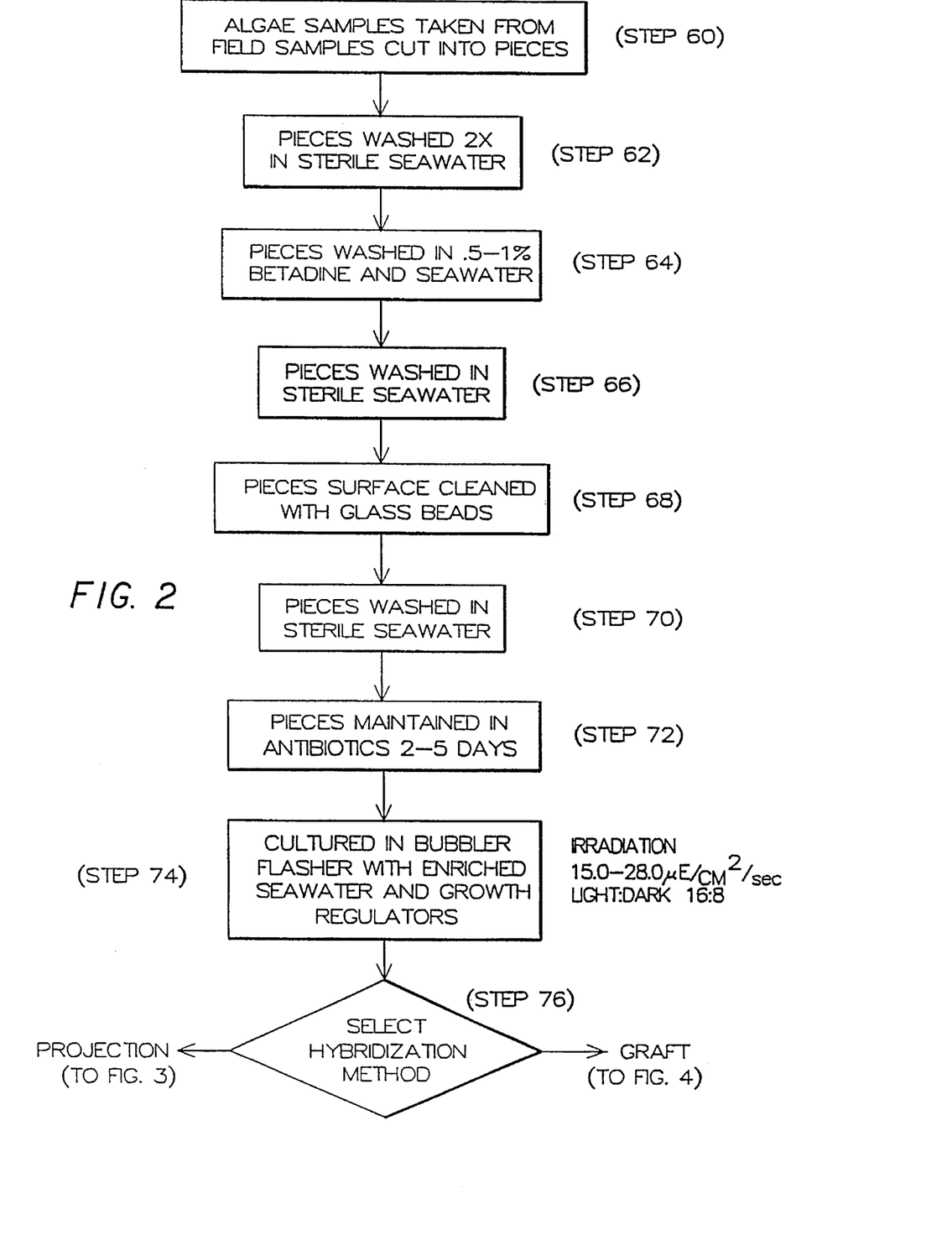
FIG. 2 is a flow chart of the initial steps in one embodiment of the method of somatic cell hybridization of the invention.

Referring to FIG. 2, the two species of non-filamentous algae which are to be hybridized are taken from the field and sliced into small pieces (step 60). The pieces are then washed once or twice in autoclaved or filter-sterilized seawater (step 62). (Seawater obtained from either sterilization technique hereinafter is referred to collectively as sterilized seawater.) The sliced algal pieces are then dipped into a 0.5–1% Betadine and seawater solution for 1–2 minutes (step 64) and the algal pieces are again rewashed with sterilized seawater (step 66).

To remove any surface contaminants from the algal pieces, a number of algal pieces are placed into a 300 ml flask with 1–3 grams of 0.5 mm diameter glass beads and a small amount of sterilized seawater. The flask containing the beads, seawater and algal pieces is then strongly shaken for several minutes (step 68).

The algal pieces are then removed from the flask, washed again three to five times with sterilized seawater (step 70), and maintained in antibiotics (in one embodiment an antibiotic mixture termed E3) for two to five days (step 72). The antibiotic mixture E3 used in the medium consists of 30 µg/ml each of polymyxin B, nalidixic acid, erythromycin, colistin, vancomycin, ampicillin, trimethoprim, and chlortetracycline.

Once the E3 antibiotic treatment of the algal pieces is complete, each algal species is incubated in a respective bubbler flask at an approximate temperature of 20° C.–29° C. (for tropical algae) in half (ESS/2) or quarter concentration (ESS/4) enriched seawater (ESS) or in ASP12 artificial seawater. In one embodiment, the plant growth regulators consist of a mixture of 5.4 nM–53.7 µM α-naphthaleneacetic acid (NAA) and 4.6 µM zeatin, with an especially preferred embodiment consisting of a final concentration of 0.01 ppm α-naphthaleneacetic acid and 0.01 ppm zeatin in the EES.

During culture in the bubbler flasks, each algal species is irradiated by cool-white fluorescent light at an intensity of 15.0–28.0 µE/cm$^2$/sec with a light:dark cycle of 16:8 hours (step 74). The algal species are allowed to grow for at least a week under these conditions to permit the plants to adapt to the environment and to insure that the plants are free of contaminants. The medium in the bubbler flasks is changed weekly. At this point, the plants to be hybridized may be selected and the method of hybridization begun.

EXAMPLE 2

Figure 3:
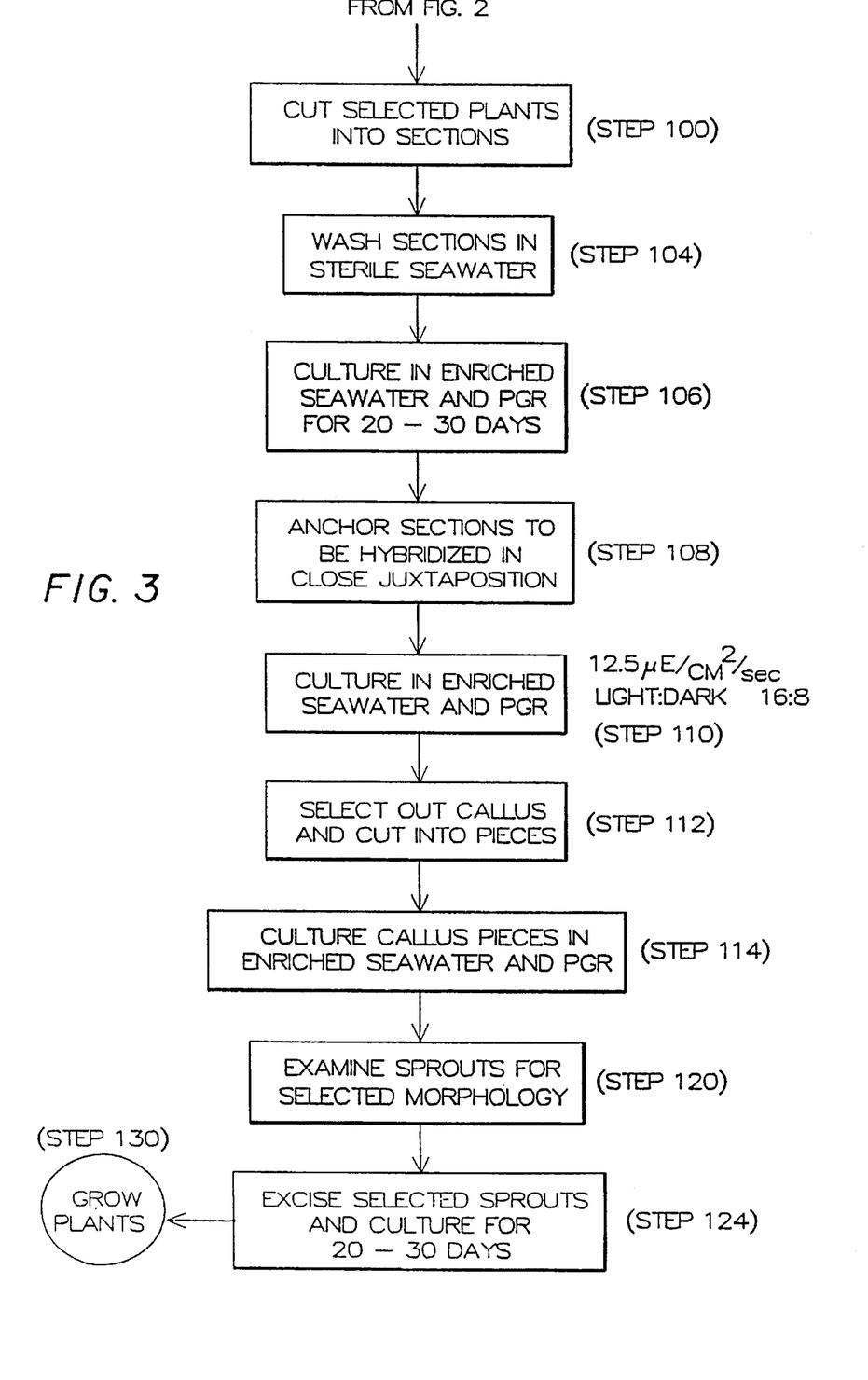
FIG. 3 is a flow chart of the steps in one embodiment of the method of the invention for the somatic cell hybridization of non-filamentous algae utilizing adjacent affixation.
Figure 3A:
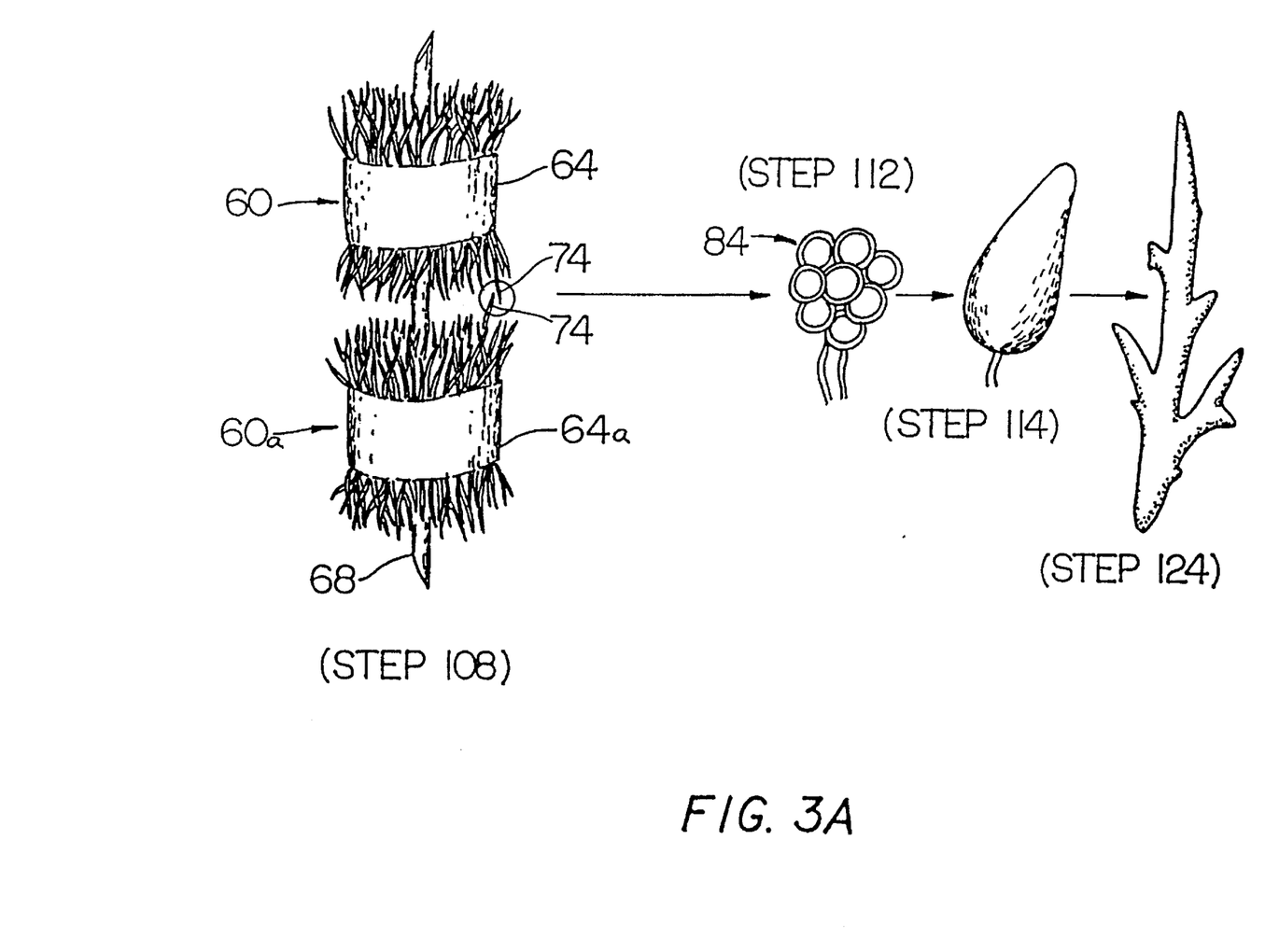
FIG. 3A is a diagrammatic representation of a number of the steps used in the embodiment of the method of somatic cell hybridization of non-filamentous algae shown in FIG. 3.

One embodiment of the method of somatic cell hybridization, referred to as close affixation is depicted in FIGS. 3 and 3a. A plant from each species to be hybridized is selected from the culture, cut into 0.3–0.6 cm long sections (step 100), and washed with sterilized seawater (step 104). These cut pieces are cultured for 20–30 days in enriched seawater (ESS/2) or ASP 12 again in the presence of plant growth regulators (step 106). At the end of the culture period, cultured pieces having a large number of cellular projections are selected from each species for hybridization.

A piece from each species 60, 60a are anchored in close juxtaposition (step 108) by placing a sharpened sterile rod 68, in one embodiment a bamboo needle, through the center of the sections 64, 64a and moving the sections 64, 64a toward one another until the sections 64, 64a are in close proximity. The sections 64, 64a are then placed in ESS/2 or ASP 12 culture medium with plant growth regulators in multiwell plates and allowed to grow at a temperature of 20°–24° C. in an incubator (step 110). The culture is irradiated by cool-white fluorescent light at an intensity of 12.25 μE/cm$^2$/sec with a light:dark cycle of 16:8 hours. The culture medium is changed weekly.

After about two months, projections 74, 74a grow from each section 64, 64a, and fuse forming hybrid heterokaryon callus like mass 84. The hybrid callus 84 is then cut into small pieces (step 112) and subcultured in ESS/2 or ASP 12 medium with plant growth regulators for about two months (step 114).

At the end of this time, shoots which grow from the callus are carefully observed (step 120) to identify hybrid plants. The hybrid somatic cell shoots are selected according to their morphology or pigmentation and/or by an infra-red or chemical carrageenan analysis of a crude preparation made from a portion of a potentially interesting plant. These hybrid shoots are then excised and cultured (step 124) in enriched seawater (ESS/2) for a month. Once the shoots grow to several mm in length, the shoots are placed in bubbler flasks and cultured (step 130).

EXAMPLE 3

Figure 4:
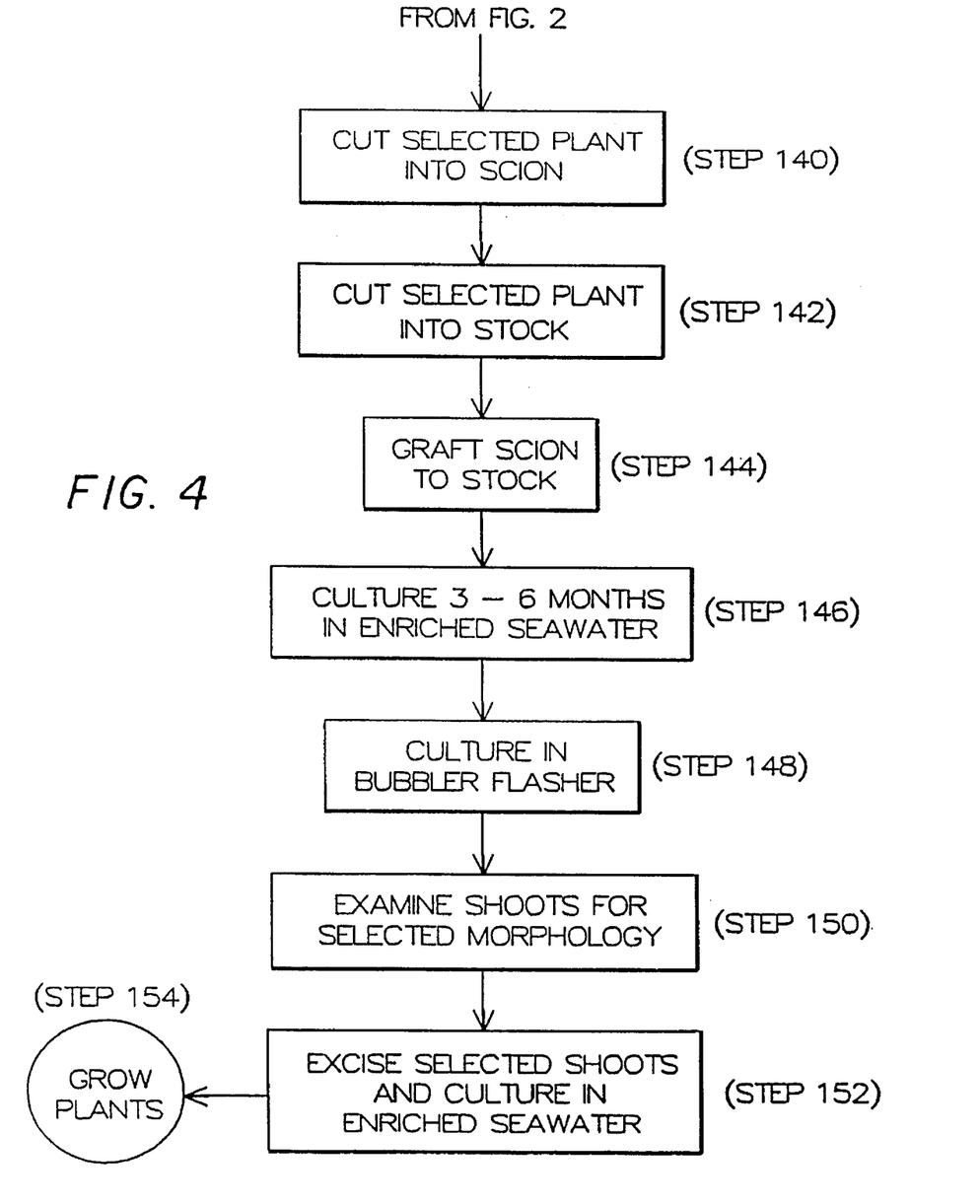
FIG. 4 is a flow chart of the steps in one embodiment of the method of the invention for the somatic cell hybridization of non-filamentous algae utilizing grafting.
Figure 4A:
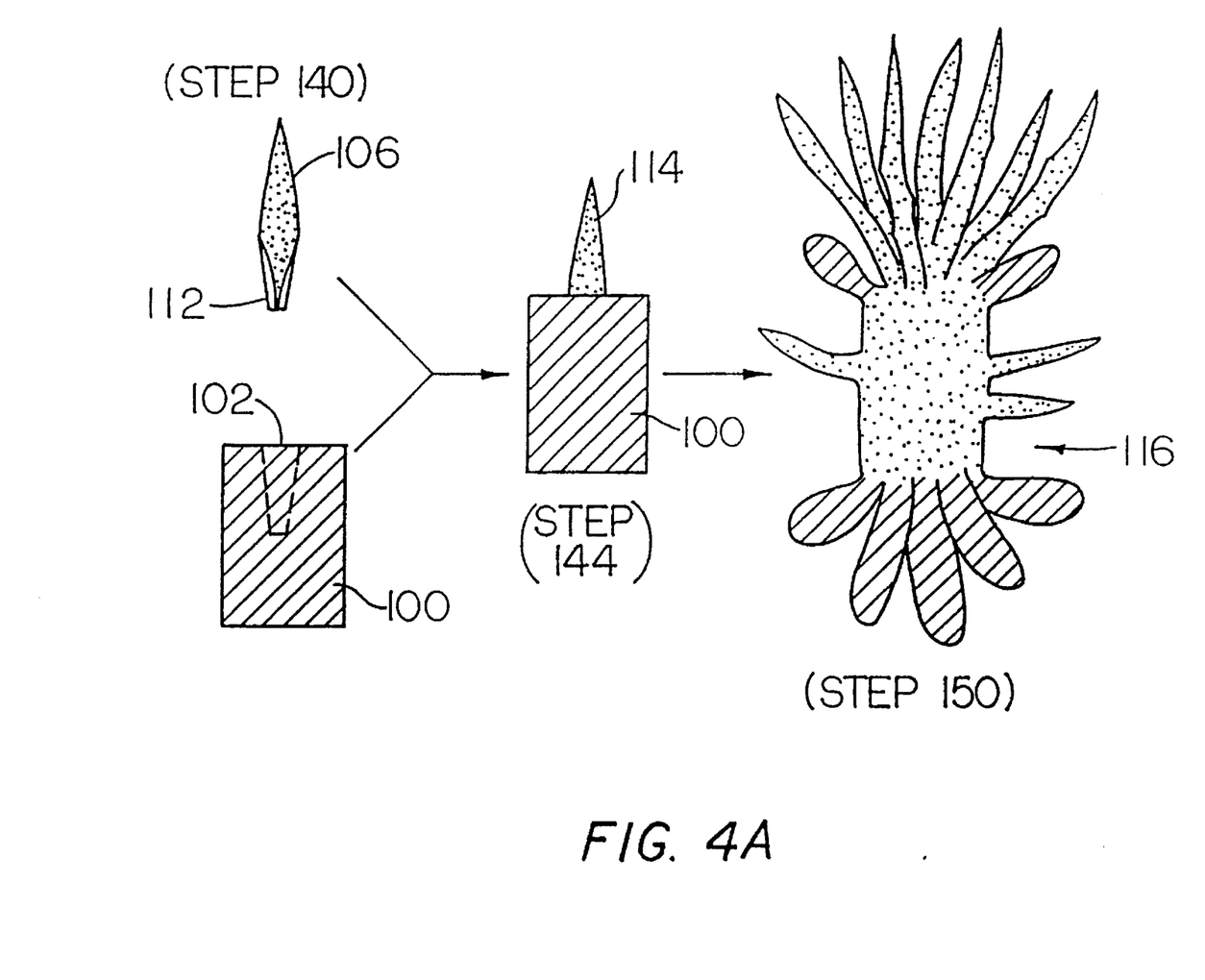
FIG. 4A is a diagrammatic representation of a number of the steps used in the embodiment of the method of somatic cell hybridization of non-filamentous algae shown in FIG. 4.

Referring to FIGS. 4 and 4a, in a second embodiment of the method of somatic cell hybridization a plant shoot from one species to be hybridized is selected from the culture and cut into a 1.0–1.5 cm long piece to form the scion 106 of the graft (step 140). The cut end of the scion 106 is further trimmed to form a wedge 112. A plant from the second species to be hybridized is selected from culture and cut into a 1.0 cm long section to form the stock 150 of the graft. (step 142). A small hole 102 is made in the center or medullary tissue of the stock section 100. The width of the hole 102 is slightly wider than the diameter of the scion and the depth of the hole 102 is a little deeper than the length of the wedge portion 112 of the scion 106.

The wedge portion 112 of the scion 114 is embedded (step 144) into the hole 102 in the stock 100 deeply enough to be held. The stock section 100 and scion 106 are then placed in ASP 12 or ESS/2 culture medium in multiwell plates and allowed to grow (step 146). The media is changed weekly and the cultures permitted to grow for 3–6 months. After this time period, the graft is transferred to T25 culture flasks with ESS/2 medium. In 1–2 months, the graft is again transferred to bubbler flasks with ESS/2 medium (step 148).

The shoots 116 which form are carefully observed (step 150) to identify hybrid plants. The hybrid somatic cell shoots are selected according to their morphology or pigmentation and/or by an infra-red or chemical carrageenan analysis of a crude preparation made from a portion of a potentially interesting plant. These hybrid shoots are then excised and cultured (step 152) in enriched seawater (ESS/ 2). Once the shoots grow to several mm in length, the shoots are placed in bubbler flasks and cultured (step 154).

EXAMPLE 4

Figures 9, 10:
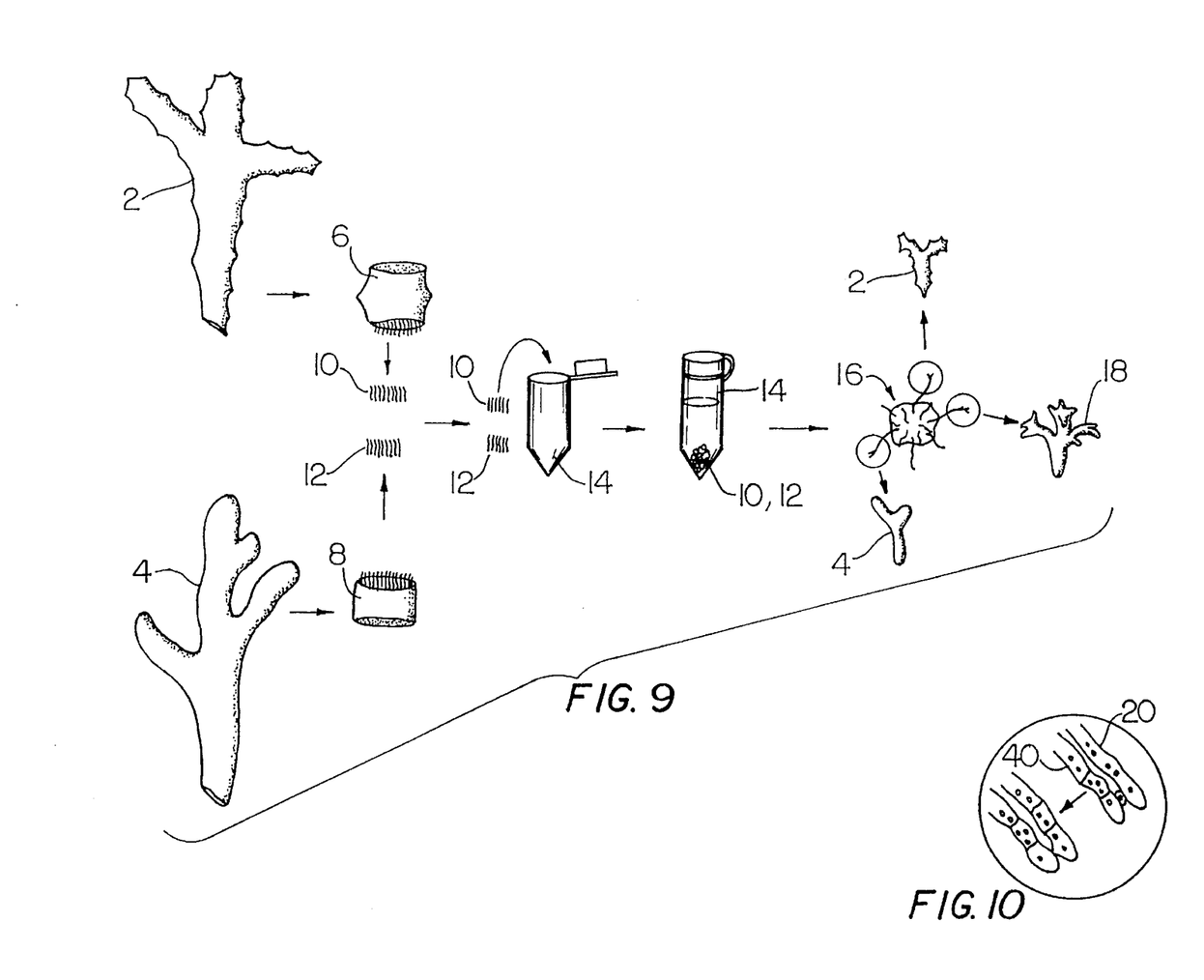
FIG. 9 is a diagrammatic representation of the steps used in yet another technique of fusing filamentous algae according to the invention.
FIG. 10 is an enlarged view of the cell-cell fusion event within the tube of FIG. 9.

Yet another embodiment of the inventive methods of producing hybrid algae is via cell-cell fusion, as shown in FIG. 9. Briefly, cross-sections 6,8 are generated by excision from each parent plant 2,4. Cellular projections 10,12 are excised from each parental cross-section 2,4, respectively, and combined in culture tube 14. The parent plant projections 20,40, respectively, are allowed to grow together to form connector cells, thus allowing for sharing of nuclei (FIG. 10). After cell-cell fusion has occurred, the mixture of cellular projections behaves as if it is a single mass or clump of cells. The clump 16 may be allowed to grow and may be cut into smaller subcultures for regeneration of shoot primordia, or cultured directly for shoot primordia formation. Regeneration and shoot primordia production are induced by altering culture conditions or exhausting culture nutrients. Whole plants may then be grown from the shoots thus produced. Parent whole plants 2,4 may be regenerated according to the procedure, along with hybrid plant 18.

This technique, described in detail below, has several advantages over those inventive methods disclosed above; for example, it saves time and effort by avoiding the delicate procedure of inserting a scion into a stock, as well as the precise holding together of two parent plant sections using a rod. All of the inventive methods, but particularly the method described in this Example, allow for greater cell-cell contact. The method described immediately below provides for actual mixing of cell projections, and thus increases the likelihood that nuclear exchange will occur between cellular projections of different plants. In addition, this technique permits the mixing together of cells from more than two species simultaneously, as well as easier microscopic observation of cell-cell fusion events. When a cell fusion event is observed, regeneration of hybrid plants can be initiated with greater likelihood of obtaining a hybrid plant. This inventive method is described in detail below.

Parent plants are cultured at 21' C. in bubbler flasks, irradiated by cool-white fluorescent light at an intensity of 25–28 μE/cm$^2$/sec with a light:dark cycle of 16:8 hours. The culture media used was half-strength enriched seawater (ESS, Saga, N., 1986, Pure Culture Algae, In: Yamada et al. (eds.) Plant Biotechnology, Tokyo Kagaku Dojin, Tokyo, JP, pp. 55–71, hereby incorporated by reference). A filter sterilized 100 ml stock solution of ESS may contain 600 mg NaNO$_3$, 80 mg Na$_2$ glycerophosphate, 40 mg sequestrene 138 Fe, 0.1 mg KI, 1000 mg Hepes-Na buffer, 40 ml P-II metals solution (Provasoli, 1964, supra), 1 ml vitamin mix, and distilled H$_2$O, pH 7.8. ESS is made by adding 10 ml ESS stock solution to 1 liter of autoclaved seawater (supplemented with 5 mg/l GeO$_2$, Lewin, 1966, Phycologia 6, 1–12, and 0.33 g/l Hepes). The pH of supplemented seawater is 7.1 before autoclaving; the final pH upon cooling is 7.8. A plant from each parent is cut into 0.3–0.6 cm thick cross-sections, which are first washed with sterilized seawater and then cultured one per well in a multi-well tissue culture plate for approximately 3 and ½ months in ASP 12 artificial seawater (Provasoli, 1964, Growing Marine Seaweeds, Proceedings International Seaweed Symposium 4:9–17, hereby incorporated by reference) plus PGRs (plant growth regulators). The plant growth regulators added may, for example, include a mixture of one or more auxins and one or more cytokinins, e.g., α-naphthaleneacetic acid (NAA) and of zeatin, such that the final concentration of each in the culture medium is approximately 0.01 ppm. Other PGRs that may be added include but are not limited to cytokinins such as kinetin, or auxins such as phenylacetic acid, 2,4,5-trichlorophenoxyacetic acid, and indoleacetic acid. See Bradley et al., 1990, Hydrobiologica 204/205:353–360.

The long cellular projections produced upon culturing each parent plant cross-section individually are removed or excised from the sections using a razor blade, and several projections from each parent are together placed in a container, e.g., a 1 ml microcentrifuge tube, using fine forceps. 0.8 ml conditioned culture media is added to the microcentrifuge tube and the tube is incubated at 21' C. under low light intensity, ca. 15 µE/cm$^2$/sec, with a light:dark cycle of 16:8 hours. The conditioned culture media comes from wells that the spinosum sections had been previously cultured in and thereby conditioned. The cellular projections tend to float slightly in the culture media. The projections are then gently pushed to the bottom of the tube using fine forceps. Alternatively, the projections may be forced to the bottom of the tube via microcentrifugation of the tube, e.g., from ca. 1 min.–30 min. Once the projections are situated on the tube bottom, they will hold each other in place in the narrow tube bottom. The purpose of using the microcentrifuge tube is to provide a means of holding the projections together in close proximity for a time sufficient to allow for connections, i.e., cell-cell fusions, to be made between parent cellular projections. Thus, any container means that allows for close contact between parental projections is useful according to this aspect of the invention.

After approximately 1 week of incubation, the cell-clump mass at the bottom of the microcentrifuge tube was gently removed from the tube and cultured in a well of a 24 multi-well tissue culture plate. In the preferred embodiment, the microcentrifuge tube is cut in half right above the narrow bottom of the tube, thus providing easy access to the cell clump to allow for gentle removal of the cell clump from the tube. It is important to avoid disturbance of the cell clump in this transfer step so as to avoid disruption of the cell-cell connections. Initially, the cell clump is cultured in conditioned culture medium. Over a period of several weeks, normal ASP12/PGR culture medium is gradually added in place of conditioned medium, thereby enriching the medium gradually. After approximately another month, the culture medium is no longer changed at all, thereby starving the culture of nutrients and depleting PGRs in order to induce regeneration and primordia shoot formation. Large numbers of primordia shoots thus are produced. The shoot primordia may be maintained in culture in bubbler flasks and allowed to grow into whole plants. IR testing may be performed at the shoot or whole plant stages.

EXAMPLE 5

The cell-cell fusion technique of the invention, as described in Example 4, was performed using a reddish/golden colored *E. spinosum* and a greenish-olive colored *E. cottonii*. Both parental plants had been in laboratory culture for some time and were thus clean of contamination. The culture conditions of the parental plants was as described. Sections of the two parental plants were made as above and incubated individually in a culture well for about 3 and ½ months along with NAA and zeatin at 0.01 ppm. The long cellular projections produced by each cultured section were excised and placed together in the bottom of a microcentrifuge tube. The projections were incubated as described above using conditioned culture medium. The cell clump that formed at the bottom of the microcentrifuge tube was carefully removed from the tube and placed in a well of a tissue culture plate with conditioned medium and replaced with normal ASP12/PGR culture medium for several more months. Regeneration of primordia shoot formation was induced by starving the culture of nutrients. Large numbers of primordia shoots were observed and maintained in bubbler flasks during growth. IR testing is then performed.

Mechanism of Fusion

Figure 6:
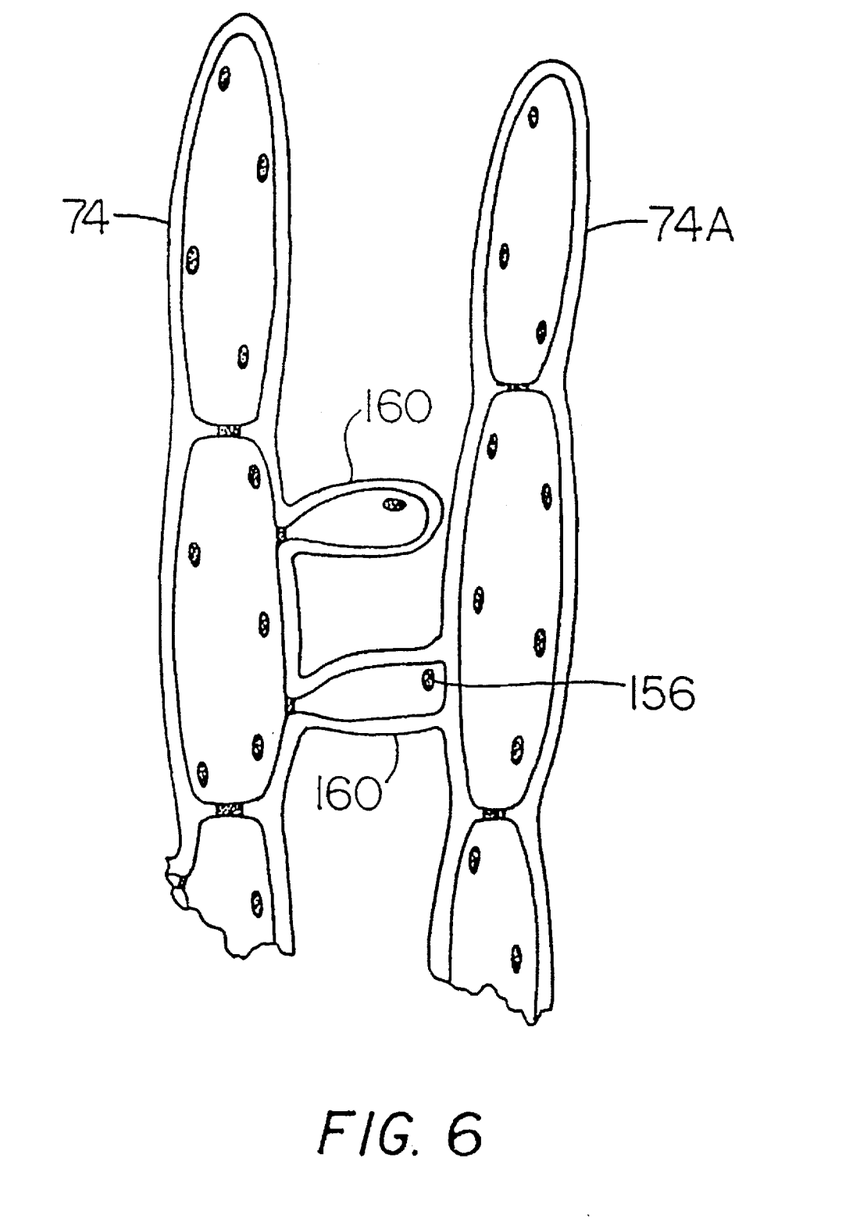
FIG. 6 is a diagrammatical representation of hybrid generation by way of conjunctor cell formation; 20

The mechanism by which the hybrid somatic cells form is not completely understood. Without being bound to any one theory, it is believed (as shown in FIG. 6) that hybrid somatic cells form as the result of the transfer of nuclei 156 from projections 74 of one species to projections 74a of the other species by way of a conjunctor cell 160. Nuclear exchange has been observed microscopically using the nuclear stain DAPI. Evidence that hybrid cells are formed may be demonstrated by isozyme protein electrophoresis, by the morphological characteristics of the plants and by the presence of the cytoplasmic incompatibility reaction (CIR) which occurs in sensitive species as a result of cell fusion. Additionally, the hybrid plants may produce phycocolloids which have a different gel strength from the phycocolloids produced by either of the parent species.

EXAMPLE 6

Figure 5:
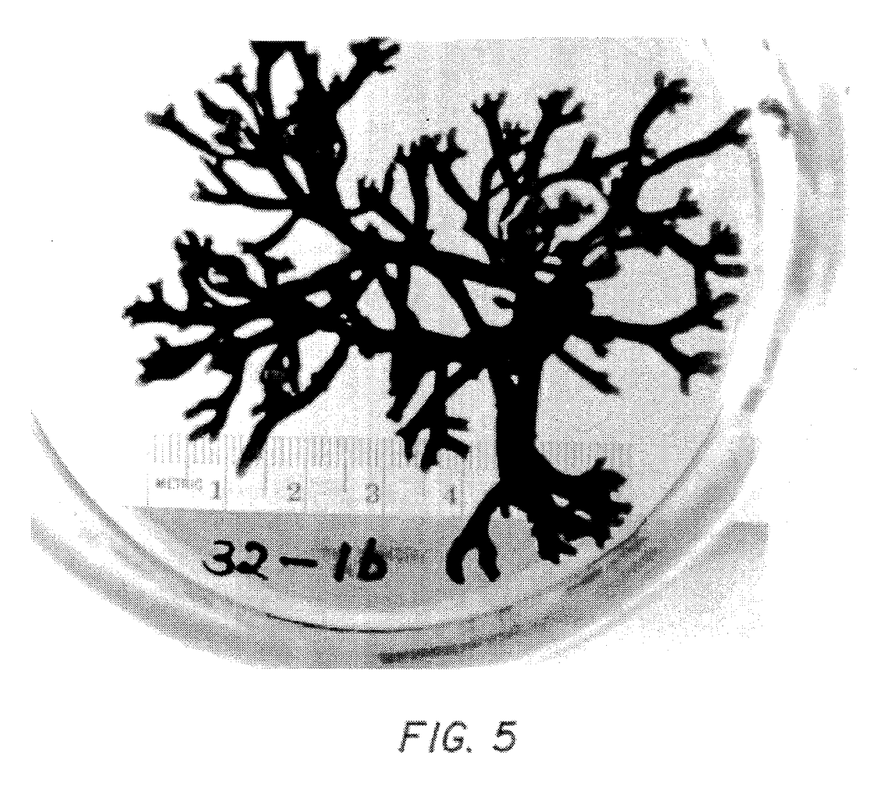
FIG. 5 is a photograph of the morphology of a hybrid of *Eucheuma spinosum* and *E. cottonii* made by the method of the invention.

The criteria (morphological, pigmentation, DNA comparisons, chemical analysis of plant components or infra-red or chemical analysis-of the carrageenan produced) by which hybrid shoots are selected for culture are determined by the charactertics (morphological, pigmentation, DNA comparisons, chemical analysis of plant components or infra-red or chemical analysis of the carrageenan produced) of the species being hybridized. For example, the hybridization of a red algal species and a greenish pigmented red algal species might result in a hybrid shoot which is reddish green. Similarly, the hybridization of an alga which has spiny features, such as *Eucheuma spinosum* (see 2 in FIG. 9), with a alga which has smooth features, such a *E. cottonii* (see 4 in FIG. 9), might result in shoots having a morphology which is intermediate between smooth and spiny features (see 18 in FIG. 9). A photograph of such a hybrid is shown in FIG. 5. Similarly, a hybrid shoot may be selected by analyzing the type of carrageenan produced; e.g., *E. cottonii* and *E. spinosum* produce κ carrageenan and ι carrageenan, respectively. Thus, an *E. cottonii/E. spinosum* hybrid will contain both κ and ι carrageenan.

Chemical Analysis of Hybrid Plants

Figure 7:
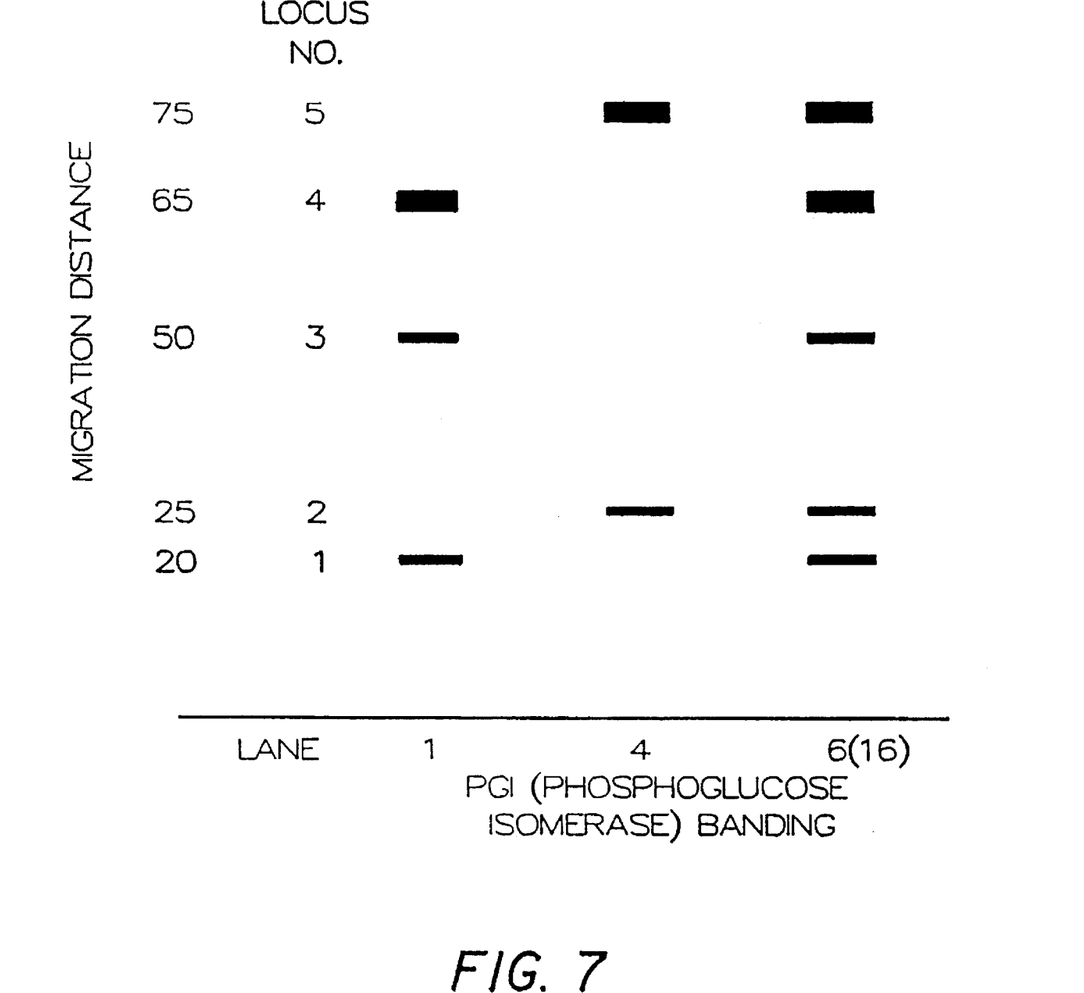
FIG. 7 is a graphical representation of the electrophoretic mobility of the enzyme phosphoglucose isomerase for *Eucheuma spinosum, E. cottonii*, and the hybrid alga made by the method of the invention as shown in FIG. 5.

An example of the chemical analysis of the plant components of a hybrid which may be considered to be illustrative of hybridization is shown in FIG. 7. In this example, the electrophoresis of the isoenzymes of phosphoglucose isomerase (PGI) from a hybrid of *Eucheuma spinosum* and *E. cottonii*, designated as E32-1b, is compared to the isoenzymes of PGI isolated from the parental stock species from which the hybrid was derived. Lane 1 shows the migration distance of the isoenzymes of PGI from *E. cottonii*. Lane 4 shows the migration distance of the isoenzymes of PGI from *Eucheuma spinosum*, and lane 6(16) shows the migration distance of the isoenzymes of PGI from a hybrid of *Eucheuma spinosum* and *E. cottonii* designated as E32-1b. As is easily seen, the isozyme pattern of the hybrid is a combination of the isozyme patterns of the species of plants from which it was derived.

Infra-red (IR) Analysis of Hybrid Plants

Additionally, a microanalytical infra-red technique may be used to screen potential hybrids for culture by comparing the relative sulfation of the carrageenan produced by each suspected hybrid to the amount of sulfation of the carrageenan produced by each parent species. The microanalytical infra-red technique may be performed on as little as 150–200 mg fresh weight (or 11–15 mg dry weight) of sample. The sample of the suspected hybrid is placed in 2 ml of H$_2$O and heated to 90° C. for four hours. The resulting mixture is cooled to 60° C. and prefiltered using mirocloth. The solution which passes through the prefilter is again filtered using a 5μ filter. The resulting carrageenan extract is poured into a mold and allowed to dry overnight at 50° C. into a film. The film is then mounted for use and its spectrum taken in an infra-red spectrometer.

Table 1 lists various peaks in the IR spectra of phycocolloids. The ratio of the intensity of the various bands of the spectra can be used to determine the chemical constituents of the phycocolloids. For example, the ratio of the intensity of the various bands of the spectrum of carrageenan can be used to determine the relative amount of sulfation of the carrageenan and hence provide an indication of the carrageenan's gel strength. Specifically, the ratio of the intensity of the 805 cm$^{-1}$ band of the infra-red spectrum which is generated by the amount of sulfate at the 3,6-anhydrogalactose 2-sulfate position of ι carrageenan to the intensity of the 850 cm$^{-1}$ band of the infra-red spectrum which is generated by the amount of sulfate at the galactose-4-sulphate position of ι and κ carrageenan has been shown to be inversely to the gel strength of the carrageenan. Thus by comparing the ratio of the 805 cm$^{-1}$/850 cm$^{-1}$ bands as produced by the suspected hybrid with the ratio as produced by each of the parents, hybrids producing an increased or different gel strength carrageenan from that produced by the parents' species can be selected. Additionally, the 830 cm$^{-1}$ is indicative of the amount of sulfation of λ carrageenan. It should be noted that other bands in the infra-red spectrum of carrageenan have been used to indicate the amount of sulfation and that other bands may be used to determine the properties of other phycocolloids, such as agar.

Figure 8:
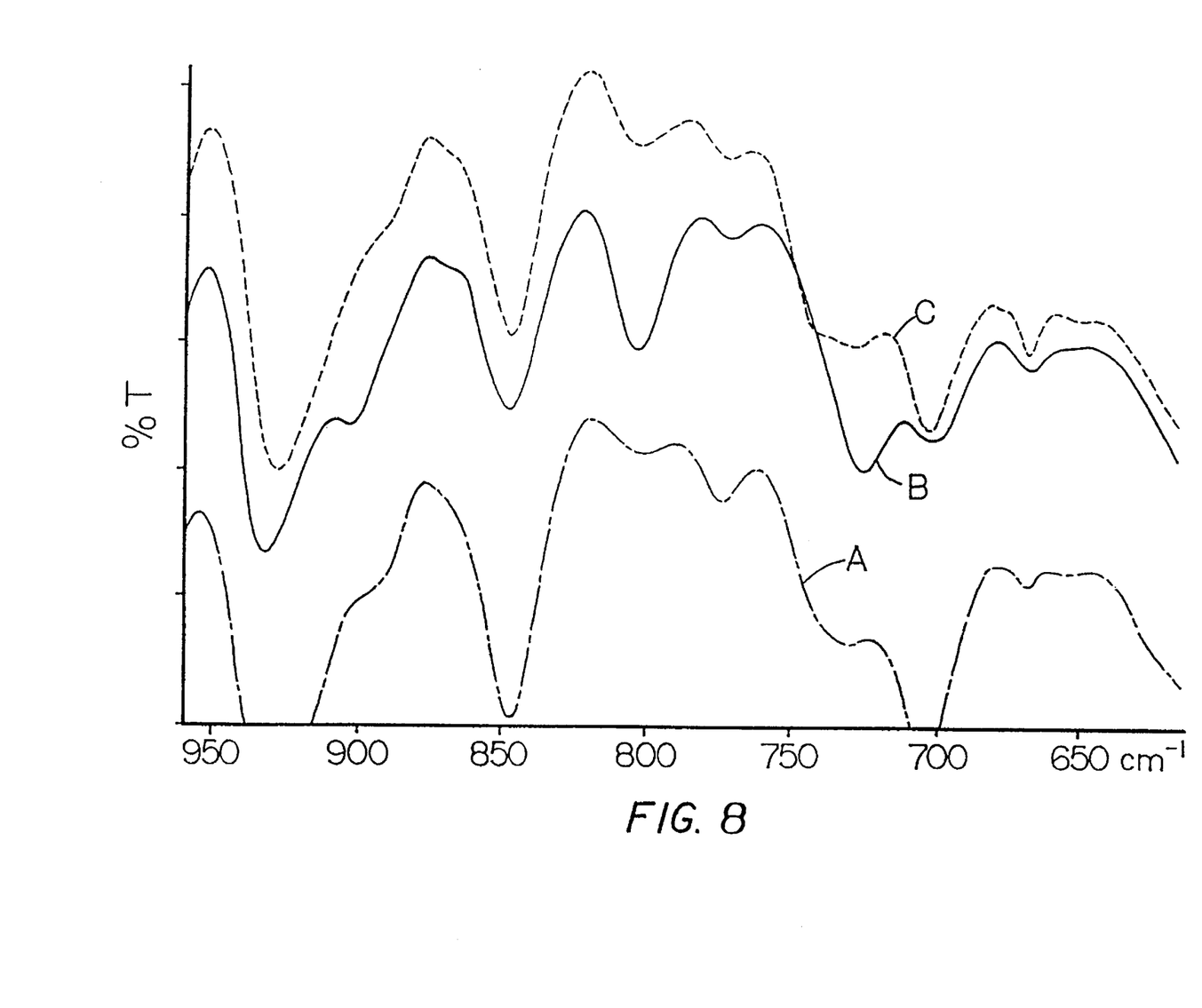
FIG. 8 depicts an infra-red spectrum taken of carrageenan produced by *E. cottonii, Eucheuma spinosum* and an infrared spectrum taken of carrageenan produced by a hybrid made by the method of the invention.

FIG. 8 depicts infra-red spectra of carrageenan produced by *E. cottonii* (Curve A) and *Eucheuma spinosum* (Curve B), taken by the above described microanalytical infra-red method and an infra-red spectrum (curve C) of carrageenan produced by a hybrid designated as E34-1'a-j. The hybrid E34-1'a-j was formed using the close affixation method of the first embodiment by closely affixing an *E. cottonii* parent species and an *Eucheuma spinosum* parent species.

The ratio of the 805 cm$^{-1}$ band to the 850 cm$^{-1}$ band for the carrageenan produced by *E. cottonii* is 0.085 while the ratio of the 805 cm$^{-1}$ band to the 850 cm$^{-1}$ band for carrageenan produced by E34-1'a-j is 0.165, indicating a significantly different degree of sulfation and hence a true hybrid. Additionally, since the hybrid has a greater 805 cm$^{-1}$ peak than *E. cottonii*, it would be expected to have a lower gel strength.

An analysis of the gel strength and gelling temperature for the carrageenan produced by the hybrid E34-1'a-j confirms the IR data discussed above. The carrageenan produced by the hybrid E34-1'a-j has a gel strength of 2510 pascals at 10° C. as measured by rheometer and a gelling temperature of 37° C. This is significantly different from the parent species *E. cottonii* which produces carrageenan which has a gel strength which ranges from 5,500–7,000 pascals and *Eucheuma spinosum* which produces carrageenan which has a gel strength of less than 200 pascals. Therefore, hybrid E34-1'a-j, which can be farmed in the tropics like *E. cottonii*, produces a carrageenan having a gel strength similar to that of carrageenan produced by *Chondrus crispus* (1,700–3,400 pascals), which can not be farmed in the tropics like *E. cottonii*.

It should be noted that the number of viable hybrids produced from a series of attempted hybridizations may be increased by the use of healthy, uncontaminated, and laboratory grown plants as the stock species from which the hybrid is created.

These and other examples of the concept of the invention illustrated above are intended by way of example and the actual scope of the invention is to be determined solely from the following claims.

TABLE 1

SIGNIFICANT BANDS IN THE INFRA-RED SPECTRA OF PHYCOCOLLOIDS

| WAVE-NUMBER CM$^{-1}$ | SOURCE MOIETY | PHYCOCOLLOID |
|---|---|---|
| 805 | 3,6-anhydro-galactose-2-sulfate | ι carrageenan |
| 820 | galactose-6-sulfate | κ, ι carrageenan precursor |
| 830 | galactose-2-sulfate | λ carrageenan |
| 845–850 | galactose-4-sulfate | κ, ι carrageenan |
| 930 | 3,6-anhydro-galactose | κ carrageenan |
| 1370 | total sulfate | carrageenan and agar |
| 2920 | total sugar content | carrageenan and agar |

We claim:

1. A method for somatic cell hybridization of two non-filamentous anatomically complex, thallophytic marine red algal species comprising the steps of:

providing a projection from each non-filamentous anatomically complex, thallophytic marine red algal species to be hybridized;

combining, in close juxtaposition in a container, said projections from each of said non-filamentous anatomically complex, thallophytic marine red algal species to be hybridized; and allowing a hybrid new shoot to form.

2. The method of claim 1 wherein said providing step comprises the steps of:

removing a section from each said non-filamentous anatomically complex, thallophytic marine red algal species to be hybridized;

culturing said sections individually until projections from each said section have formed; and excising a said projection from each said non-filamentous anatomically complex, thallophytic marine red algal species to be hybridized.

3. The method of claim 2 wherein prior to removing said section from each non-filamentous anatomically complex, thallophytic marine red algal species to be hybridized, each said species to be hybridized is washed two to five times with sterilized seawater and placed in an antibiotic and medium mixture for between two and five days.

4. The method of claim 3 wherein after said species to be hybridized are placed in an antibiotic and medium mixture for between two and five days and before removing said section from each non-filamentous anatomically complex, thallophytic marine red algal species to be hybridized, each said species is cultured in enriched seawater.

5. The method of claim 1, said species to be hybridized being *Eucheuma cottonii* and *Eucheuma spinosum*.

6. A non-filamentous anatomically complex, thallophytic marine red hybrid algal plant formed from somatic cell hybridization of two non-filamentous marine red algal species, by a method of hybridization comprising the steps of:

removing a section from each said non-filamentous anatomically complex, thallophytic marine red algal species to be hybridized;

anchoring, in close juxtaposition, each said section from each of said species to be hybridized;

culturing said sections in close juxtaposition until projections from each said section have fused with projections from each said other section to form hybrid new shoots; and isolating said hybrid new shoots so formed.

7. A non-filamentous anatomically complex, thallophytic marine red hybrid algal plant formed from somatic cell hybridization of two non-filamentous anatomically complex, thallophytic marine red algal species, by a method of hybridization comprising the steps of:

providing a projection from each non-filamentous anatomically complex, thallophytic marine red algal species to be hybridized;

combining, in close juxtaposition in a container, said projections from each of said algal species to be hybridized; and allowing a hybrid new shoot to form.

8. A non-filamentous anatomically complex, thallophytic marine red hybrid algal plant formed from somatic cell hybridization of two non-filamentous anatomically complex, thallophytic marine red algal species, by a method of hybridization comprising the steps of:

removing a stock section from one non-filamentous anatomically complex, thallophytic marine red algal species to be hybridized;

removing a tip from a second species;

cutting said tip to make an insertion portion to said tip;

embedding said insertion portion of said tip into said stock section;

culturing said tip and said stock section until hybrid new shoots grow from said stock section and tip; and isolating said hybrid new shoots so formed.

9. The non-filamentous anatomically complex, thallophytic marine red hybrid algal plant of claim 7, formed from somatic cell hybridization of *Eucheuma cottonii* and *Eucheuma spinosum*.

10. A process for producing carrageenan from a marine hybrid red algal plant, comprising the steps of:

removing a section from each marine red algal species to be hybridized;

anchoring, in close juxtaposition, each said section from each of said marine red algal species to be hybridized;

culturing said sections in close juxtaposition until projections from each said section have fused with projections from each said other section forming hybrid new shoots;

isolating said hybrid new shoots so formed;

growing hybrid multicellular material from said hybrid new shoots; and processing said hybrid multicellular material to recover carrageenan.

11. A process for producing carrageenan from a marine hybrid red algal plant, comprising the steps of:

providing a projection from each marine red algal species to be hybridized;

combining, in close juxtaposition in a container, said projections from each of said marine algal species to be hybridized;

allowing a hybrid new shoot to form;

growing hybrid multicellular material from said hybrid new shoots; and processing said hybrid multicellular material to recover carrageenan.

12. A process for producing carrageenan from a marine hybrid red algal plant, comprising the steps removing a stock section from one marine red algal species to be hybridized;

removing a tip from a second species;

cutting said tip to make an insertion portion to said tip;

embedding said insertion portion of said tip into said stock section;

culturing said tip and said stock section until hybrid new shoots grow from said stock section and tip;

isolating said hybrid new shoots so formed;

growing hybrid multicellular material from said hybrid new shoots; and processing said hybrid multicellular material to recover carrageenan.

* * * * *